United States Patent
Choi et al.

(10) Patent No.: US 9,936,865 B2
(45) Date of Patent: Apr. 10, 2018

(54) FIBER SCANNING OPTICAL PROBE AND MEDICAL IMAGING APPARATUS INCLUDING THE SAME

(71) Applicants: SAMSUNG ELECTRONICS CO., LTD., Suwon-si (KR); KOREA ADVANCED INSTITUTE OF SCIENCE AND TECHNOLOGY, Daejeon-si (KR)

(72) Inventors: Min-seog Choi, Seoul (KR); Ki-Hun Jeong, Daejeon-si (KR); Hyeon-Cheol Park, Daejeon-si (KR); Seun-wan Lee, Suwon-si (KR)

(73) Assignees: SAMSUNG ELECTRONICS CO., LTD., Suwon-si (KR); KOREA ADVANCED INSTITUTE OF SCIENCE AND TECHNOLOGY, Daejeon-si (KR)

(*) Notice: Subject to any disclaimer, the term of this patent is extended or adjusted under 35 U.S.C. 154(b) by 811 days.

(21) Appl. No.: 14/513,448

(22) Filed: Oct. 14, 2014

(65) Prior Publication Data

US 2015/0126858 A1    May 7, 2015

(30) Foreign Application Priority Data

Nov. 6, 2013    (KR) .................. 10-2013-0134369

(51) Int. Cl.
*G02B 6/06* (2006.01)
*A61B 1/07* (2006.01)
*A61B 5/00* (2006.01)
*A61B 1/00* (2006.01)
*G02B 23/26* (2006.01)
*G02B 26/10* (2006.01)

(52) U.S. Cl.
CPC ............ *A61B 1/07* (2013.01); *A61B 1/00172* (2013.01); *A61B 5/0066* (2013.01); *A61B 5/0095* (2013.01); *A61B 5/6873* (2013.01); *G02B 23/26* (2013.01); *G02B 26/103* (2013.01)

(58) Field of Classification Search
CPC ..... A61B 5/0095; A61B 5/444; A61B 5/0066; A61B 5/72
See application file for complete search history.

(56) References Cited

U.S. PATENT DOCUMENTS

| | | | |
|---|---|---|---|
| 4,410,235 A | 10/1983 | Klement et al. | |
| 7,608,842 B2 | 10/2009 | Johnston | |
| 8,537,203 B2* | 9/2013 | Seibel | A61B 1/0008 348/45 |
| 9,420,954 B2* | 8/2016 | Choi | A61B 5/0095 |
| 9,642,646 B2* | 5/2017 | Patel | A61B 17/320758 |

(Continued)

*Primary Examiner* — Ellen Kim
(74) *Attorney, Agent, or Firm* — Sughrue Mion, PLLC

(57) ABSTRACT

Fiber scanning optical probes and medical imaging apparatuses including the same are provided. The fiber scanning optical probe includes an optical fiber; an actuator attached onto the optical fiber and configured to drive the optical fiber at a driving resonance frequency; a mass provided at a side of the optical fiber and configured to control the driving resonance frequency; and a frequency separator provided on a portion of the optical fiber between the actuator and the mass, the frequency separator being configured to separate the driving resonance frequency into separate resonance frequencies.

21 Claims, 5 Drawing Sheets

(56) References Cited

U.S. PATENT DOCUMENTS

| | | | | |
|---|---|---|---|---|
| 2002/0064341 A1* | 5/2002 | Fauver | ............... | G02B 6/241 |
| | | | | 385/25 |
| 2007/0270650 A1* | 11/2007 | Eno | ............... | A61B 1/00045 |
| | | | | 600/145 |
| 2009/0208143 A1* | 8/2009 | Yoon | ............... | A61B 1/0058 |
| | | | | 382/321 |
| 2010/0280534 A1* | 11/2010 | Sher | ............. | A61B 17/320758 |
| | | | | 606/159 |
| 2017/0010461 A1* | 1/2017 | Kasai | ............... | G02B 23/2423 |

\* cited by examiner

FIBER SCANNING OPTICAL PROBE AND MEDICAL IMAGING APPARATUS INCLUDING THE SAME

CROSS-REFERENCE TO RELATED APPLICATION

This application claims the benefit of Korean Patent Application No. 10-2013-0134369, filed on Nov. 6, 2013, in the Korean Intellectual Property Office, the disclosure of which is incorporated herein in its entirety by reference.

BACKGROUND

1. Field

The exemplary embodiments relate to fiber scanning optical probes and medical imaging apparatuses including the same, and more particularly, to fiber optical probes for controlling light paths by deforming fibers and medical imaging apparatuses including the same.

2. Description of the Related Art

In the medical imaging field, demands are being made for a technique for obtaining surface information regarding a human body or skin tissues and obtaining tomography images of portions therebelow. Particularly, most cancers start below epithelial cells and spread into hypodermal cells where blood vessels are located. Therefore, if cancers can be found in early stages, damages due to cancers may be significantly reduced. Although tomography images may be obtained by using imaging techniques in the related art including magnetic resonance imaging (MRI), computed tomography (CT) imaging, or ultrasonography, it is difficult to detect small cancers in early stages therewith due to low resolutions of these imaging techniques. Meanwhile, unlike the techniques in the related art, recently introduced techniques including optical coherence tomography (OCT), optical coherence microscopy (OCM), and photoacoustic tomography (PAT) use lights. Therefore, skin penetrating depths of the above-stated recently introduced techniques are from about 1 mm to 2 mm (OCT) and from about 30 mm to about 50 mm (PAT), for example. However, resolutions of images obtained by using the above-stated techniques are about 10 times higher than the resolution of an image obtained by using ultrasonography. Therefore, the techniques are expected to be useful for finding cancers in early stages.

To apply such an optical medical imaging technique for diagnosis of an interior of a human body (e.g., an endoscope, a laparoscope, a surgery robot, etc.), it is necessary to receive light from a light source and transmit the light into a human body, and for this purpose, an optical probe may be used. An optical probe includes a series of optical lenses for focusing light at a particular distance and an optical scanning element for irradiating light to a particular region. The optical scanning element may control a path of light by changing a tilting angle of a reflective mirror, such as a micro-electro mechanical system (MEMS) mirror, or may control a path of light by physically deforming an optical fiber.

SUMMARY

Provided are fiber optical probes for controlling paths of light by deforming fibers and medical imaging apparatuses including the same.

Additional aspects will be set forth in part in the description which follows and, in part, will be apparent from the description, or may be learned by practice of the exemplary embodiments.

According to an aspect of an exemplary embodiment, there is provided a fiber scanning optical probe including an optical fiber; an actuator attached onto the optical fiber and configured to drive the optical fiber at a driving resonance frequency; a mass provided at a side of the optical fiber and configured to control the driving resonance frequency; and a frequency separator provided on a portion of the optical fiber between the actuator and the mass, the frequency separator being configured to separate the driving resonance frequency into separate resonance frequencies.

The actuator is configured to drive the optical fiber in two axial directions, and the frequency separator is configured to separate the resonance frequencies in the two axial directions to be different from each other. The frequency separator is configured to control bending moments of inertia in the two axial directions to be different from each other. The frequency separator includes a non-axisymmetric structure having different cross-sectional shapes in the two axial directions.

The optical fiber is configured to pass through the non-axisymmetric structure. The non-axisymmetric structure is formed of a single body. The non-axisymmetric structure includes at least two bodies that are spaced apart from each other. The fiber scanning optical probe further includes at least one connecting member interconnecting the at least two bodies. The nonaxisymmetric structure includes silicon, a polymer, or a metal. The mass has a same cross-sectional shape in the two axial directions. The actuator includes a piezoelectric actuator.

The fiber scanning optical probe further includes a probe housing including a light input unit configured to input light into the optical fiber, and a light output unit configured to output the light from the optical fiber, where the optical fiber, the actuator, and the frequency separator are provided in the probe housing. The fiber scanning optical probe further includes a lens unit provided inside the probe housing on a light traveling path between the light input unit and the light output unit, the lens unit including at least one lens. The fiber scanning optical probe further includes a light traveling path changing member which is provided between the lens unit and the light output unit. The light traveling path changing member includes a prism or a reflection mirror.

According to another aspect of an exemplary embodiment, there is provided a medical imaging apparatus including a light source configured to irradiate light; a fiber scanning optical probe configured to scan a target object by using the light from the light source; a receiver configured to receive a signal from the target object; and a signal processor configured to generate an image signal by processing the signal received by the receiver, where the fiber scanning optical probe includes an optical fiber; an actuator attached onto the optical fiber and configured to drive the optical fiber at a driving resonance frequency; a mass provided at a side of the optical fiber and configured to control the driving resonance frequency; and a frequency separator provided on a portion of the optical fiber between the actuator and the mass and configured to separate the driving frequency into separate resonance frequencies.

The signal processed by the signal processor is a signal generated according to one of optical coherence tomography (OCT), optical coherence microscopy (OCM), or photoacoustic tomography (PAT).

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
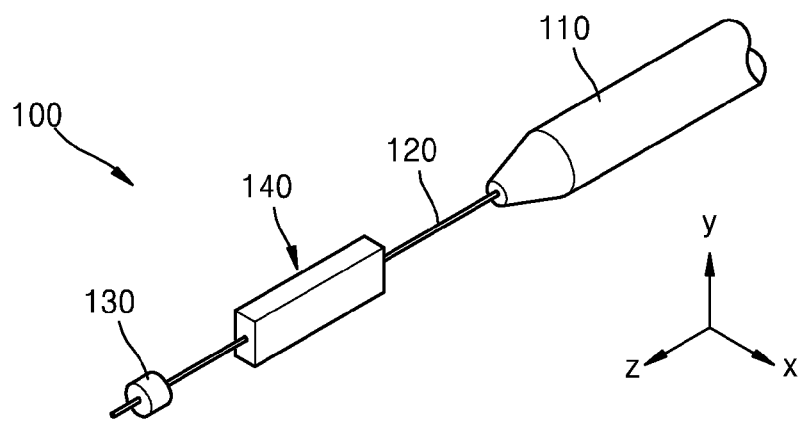
FIG. 1 is a perspective view of a fiber scanning optical probe according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the exemplary embodiments.

FIG. 1 is a perspective view of a fiber scanning optical probe 100 according to an exemplary embodiment.

Referring to FIG. 1, the fiber scanning optical probe 100 includes an optical fiber 120, an actuator 110 for driving the optical fiber 120, a mass 130 arranged at a side of the optical fiber 120, and a frequency separator 140 arranged on a portion of the optical fiber 120 between the actuator 110 and the mass 130.

The fiber scanning optical probe 100 scans light to a desired region by inducing deformation of the optical fiber 120. To this end, the actuator 110 for deforming the optical fiber 120 is attached to the optical fiber 120. The actuator 110 may drive the optical fiber 120, such that an end of the optical fiber 120 is deformed in two axial directions (e.g., the x-axis direction and the y-axis direction in FIG. 1). According to an exemplary embodiment, the two axial directions may be perpendicular to each other. However, the exemplary embodiments are not limited thereto. Also, the actuator 110 may be, for example, a piezoelectric actuator including a piezoelectric material that is deformed due to an electric signal.

Figure 2:
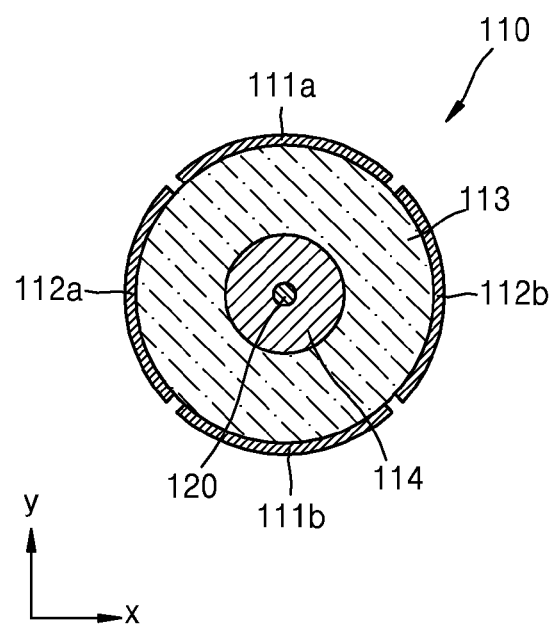
FIG. 2 is a cross-sectional view of an actuator shown in FIG. 1.

FIG. 2 is a cross-sectional view of the actuator 110 shown in FIG. 1. FIG. 2 shows a case where the actuator 110 is a piezoelectric actuator. Referring to FIG. 2, the actuator 110 has a circular cross-sectional shape. In detail, the actuator 110 includes a piezoelectric material layer 113 having a circular cross-section and electrodes 111a, 111b, 112a, and 112b arranged on the piezoelectric material layer 113. In the piezoelectric material layer 113, the optical fiber 120 and a protection layer 114 for protecting the optical fiber 120 are arranged. The piezoelectric material layer 113 is arranged to surround the protection layer 114, and the electrodes 111a, 111b, 112a, and 112b are arranged on the outer surfaces of the piezoelectric material layer 113.

The electrodes 111a, 111b, 112a, and 112b include a pair of first and second electrodes 111a and 111b, which are respectively arranged on the top surface and the bottom surface of the piezoelectric material layer 113, and a pair of third and fourth electrodes 112a and 112b, which are respectively arranged on two opposite side surfaces of the piezoelectric material layer 113. According to an exemplary embodiment, when an electric signal is applied between the first and second electrodes 111a and 111b, an end of the optical fiber 120 may be deformed in a vertical direction (that is, the y-axis direction of FIG. 2) due to deformation of the piezoelectric material layer 113. Furthermore, when an electric signal is applied to between the third and fourth electrodes 112a and 112b, an end of the optical fiber 120 may be deformed in a horizontal direction (that is, the x-axis direction of FIG. 2) due to deformation of the piezoelectric material layer 113. As described above, the actuator 110 may manipulate the optical fiber 120 in two axial directions (e.g., the x-axis direction and the y-axis direction).

Figure 3:
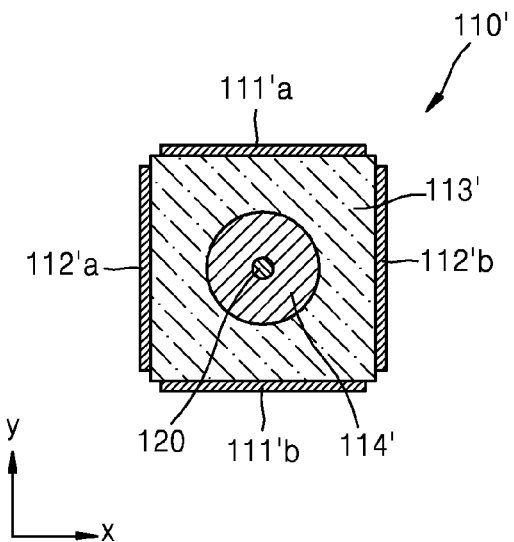
FIG. 3 shows an actuator, which is a modification of the actuator of FIGS. 1 and 2.

FIG. 3 shows an actuator 110', which is a modification of the actuator 110 of FIG. 1. Referring to FIG. 3, the actuator 110' has a rectangular cross-sectional shape. The actuator 110' includes a piezoelectric material layer 113' having a rectangular shape and electrodes 111'a, 111'b, 112'a, and 112'b arranged on the piezoelectric material layer 113. In the piezoelectric material layer 113', the optical fiber 120 and a protection layer 114' for protecting the optical fiber 120 are arranged. The piezoelectric material layer 113' is arranged to surround the protection layer 114', and the electrodes 111'a, 111'b, 112'a, and 112'b are arranged on the outer surfaces of the piezoelectric material layer 113'.

The electrodes 111'a, 111'b, 112'a, and 112'b include a pair of first and second electrodes 111'a and 111'b, which are respectively arranged on the top surface and the bottom surface of the piezoelectric material layer 113', and a pair of third and fourth electrodes 112'a and 112'b, which are respectively arranged on two opposite side surfaces of the piezoelectric material layer 113'. As described above, the first and second electrodes 111'a and 111'b are electrodes which deform the optical fiber 120 in a vertical direction (that is, the y-axis direction of FIG. 3), whereas the third and fourth electrodes 112'a and 112'b are electrodes which deform the optical fiber 120 in a horizontal direction (that is, the x-axis direction of FIG. 3). Further, although examples in which the actuator 110 or 110' have a circular or a rectangular cross-sectional shape are described above, actuators having various other shapes (e.g., triangular, polygonal, combinations of various shapes, etc.) may be used according to other exemplary embodiments.

Referring back to FIG. 1, the optical fiber 120 is driven by the actuator 110 and transmits light from an external light source to a target object and may include a single mode optical fiber, for example. The mass 130 is arranged at a side of the optical fiber 120 (e.g., an end portion of the optical fiber 120). A through hole (not shown) may be formed in the mass 130, such that the optical fiber 120 may pass therethrough. The mass may have same cross-sectional shapes in two axial directions (e.g., the x-axis direction and the y-axis direction shown in FIG. 1). The mass 130 controls resonance frequency of the optical fiber 120 due to mass of the mass 130. In other words, if the mass 130 is arranged at a side of the optical fiber 120, a resonance frequency of the optical fiber 120 decreases due to mass of the mass 130, and thus the actuator 110 may efficiently manipulate the optical fiber 120. In this case, resonance frequency of the optical fiber 120 to which the mass 130 is attached may be determined according to a length and diameter of the optical fiber 120 and a mass of the mass 130. FIG. 1 shows an example in which the mass 130 has a circular cross-sectional shape. The mass 130 may also have various other cross-sectional shapes. The mass 130 may be formed of a material that may be easily worked or manipulated, e.g., silicon, a polymer, or a metal. However, the exemplary embodiments are not limited thereto, and the mass 130 may be formed of any of various other types of materials. Furthermore, FIG. 1 shows an example in which the mass 130 is a single structure. However, the mass 130 may also include a plurality of structures.

A frequency separator 140 for separating resonance frequency is arranged on a portion of the optical fiber 120 between the actuator 110 and the mass 130. The frequency separator 140 separates resonance frequencies in two axial directions (e.g., the x-axis direction and the y-axis direction shown in FIG. 1) while the optical fiber 120 to which the mass 130 is attached is driven. To this end, the frequency separator 140 may be implemented as a non-axisymmetric structure having different cross-sectional shapes in two axial directions.

Generally, in case of performing a scanning operation by driving the optical fiber 120, the actuator 110 drives the optical fiber 120 at the resonance frequency (e.g., driving resonance frequency) of a fiber-actuator system or a frequency domain near the resonance frequency for maximum efficiency. According to an exemplary embodiment, the term 'fiber-actuator system' may refer to the actuator 110 and all structures driven by the actuator 110. During a scanning operation, if resonance frequencies in the two axial directions in which the optical fiber 120 is driven are identical to each other, a coupling effect occurs between the two axial directions, and thus, it is difficult to secure a precise scanning path. Since resonance frequency of a fiber-actuator system is proportional to a bending moment of inertia, resonance frequencies in the two axial directions may become different from each other when bending moments of inertia in the two axial directions are different from each other. Therefore, according to the present exemplary embodiment, the frequency separator 140 implemented as a non-axisymmetric structure for controlling bending moments of inertia in the two axial directions to be different from each other is arranged on the optical fiber 120, thereby making resonance frequencies in the two axial directions different from each other.

Figure 4:
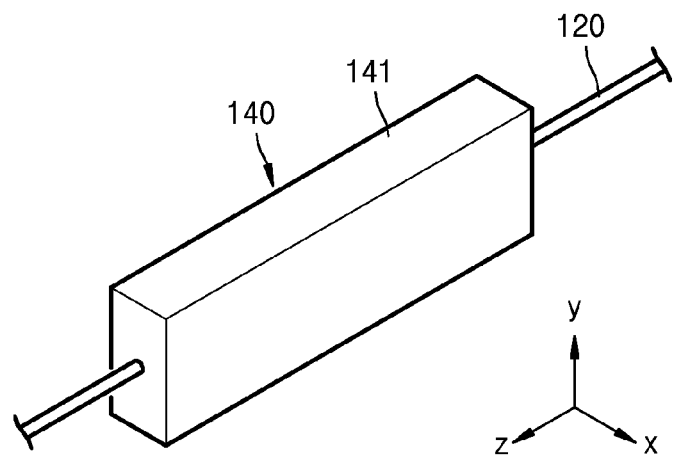
FIG. 4 is a diagram showing the frequency separator shown in FIG. 1 in close detail.

FIG. 4 is a diagram showing the frequency separator 140 shown in FIG. 1 in close detail. Referring to FIG. 4, the frequency separator 140 is implemented as the non-axisymmetric structure for making bending moments of inertia in two axial directions (e.g., the x-axis direction and the y-axis direction) different from each other. To this end, the frequency separator 140 may have cross-sectional shapes different from each other in the two axial directions. The non-axisymmetric structure may be implemented as one body 141. Furthermore, a through hole (not shown) in which the optical fiber 120 passes through may be formed in the body 141. The body 141 may be formed of a material that may be easily worked or manipulated, e.g., silicon, a polymer, or a metal. However, the exemplary embodiments are not limited thereto. Further, FIG. 4 shows an example case in which the frequency separator 140 implemented as the non-axisymmetric structure includes the body 141 having a rectangular cross-sectional shape. Furthermore, the frequency separator 140 implemented as the non-axisymmetric structure may include a body having any of various cross-sectional shapes, such as a circular cross-sectional shape, an elliptical cross-sectional shape, or a polygonal cross-sectional shape. If the body has a circular or right-polygonal cross-sectional shape, a through hole in which an optical fiber passes may be formed at a location offset from the center of the body.

Figure 5:
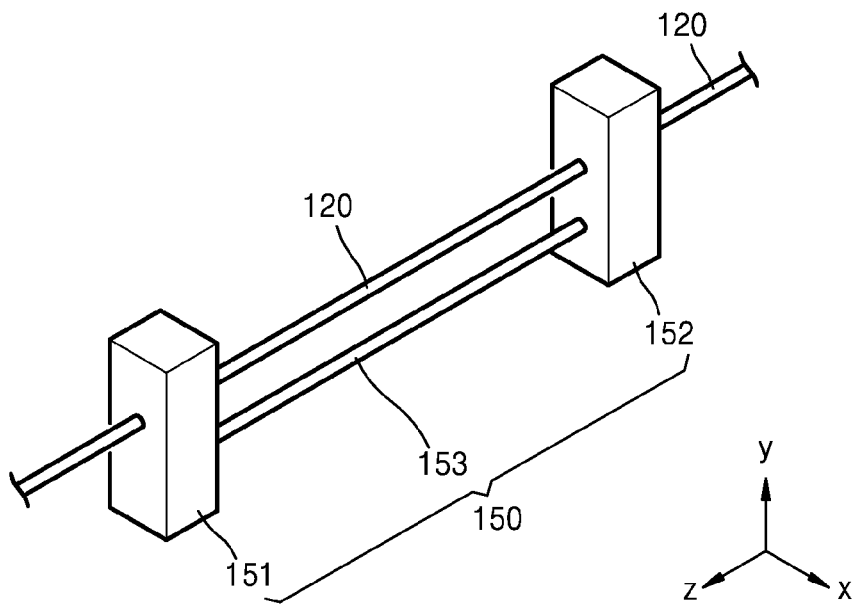
FIG. 5 is a diagram showing a modified example of the frequency separator shown in FIG. 1.

FIG. 5 is a diagram showing a modified example of the frequency separator shown in FIG. 1. Referring to FIG. 5, the frequency separator 150 includes a non-axisymmetric structure for making bending moments of inertia in two axial directions (e.g., the x-axis direction and the y-axis direction) different from each other. To this end, the frequency separator 150 including the non-axisymmetric structure may have cross-sectional shapes different from each other in the two axial directions. According to the present exemplary embodiment, the frequency separator 150 including the non-axisymmetric structure may include first and second bodies 151 and 152 arranged on the optical fiber 120 and spaced apart from each other. Through holes (not shown) in which the optical fiber 120 passes may be formed in the first and second bodies 151 and 152. The first and second bodies 151 and 152 may be formed of a material that may be easily worked or manipulated, e.g., silicon, a polymer, or a metal. However, the exemplary embodiments are not limited thereto. Furthermore, the frequency separator 150 may include a connecting member 153 interconnecting the first and second bodies 151 and 152 and arranged between the first and second bodies 151 and 152. Although a case in which the frequency separator 150 having the non-axisymmetric structure including the two bodies 151 and 152 arranged to be spaced apart from each other is described above, the exemplary embodiments are not limited thereto, and the frequency separator 150 may also include three or more bodies.

Figure 6:
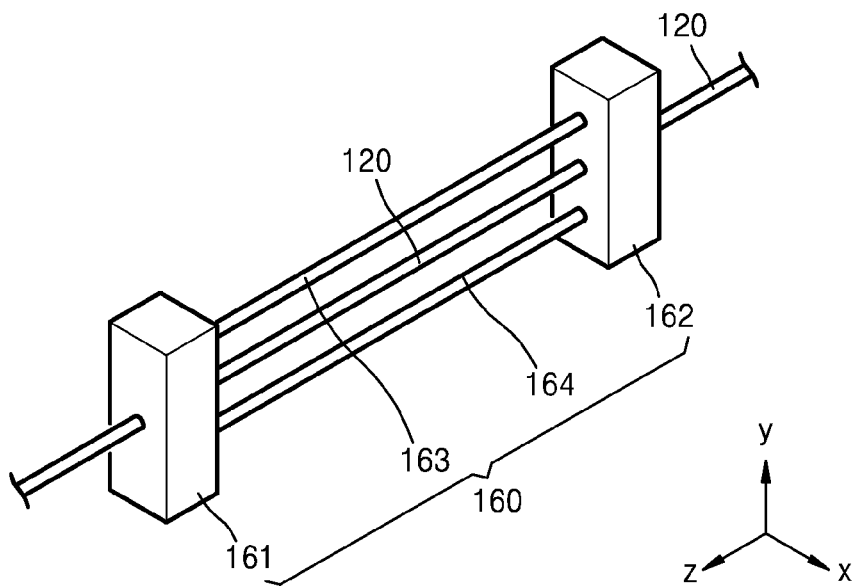
FIG. 6 is a diagram showing another modified example of the frequency separator shown in FIG. 1.

FIG. 6 is a diagram showing another modified example of the frequency separator shown in FIG. 1. Referring to FIG. 6, the frequency separator 160 includes a non-axisymmetric structure for making bending moments of inertia in two axial directions (e.g., the x-axis direction and the y-axis direction) different from each other. To this end, the frequency separator 160 including the non-axisymmetric structure may have cross-sectional shapes different from each other in the two axial directions. According to the present exemplary embodiment, the frequency separator 160 including the non-axisymmetric structure may include first and second bodies 161 and 162 arranged on the optical fiber 120 and spaced apart from each other and first and second connecting members 163 and 164 interconnecting the first and second bodies 161 and 162. Through holes (not shown) through which the optical fiber 120 passes may be formed in the first and second bodies 161 and 162. The first and second bodies 161 and 162 may be formed of a material that may be easily worked, e.g., silicon, a polymer, or a metal. However, the exemplary embodiments are not limited thereto. The first connecting member 163 may interconnect upper portions of the first and second bodies 161 and 162, whereas the second connecting member 164 may interconnect lower portions of the first and second bodies 161 and 162. Although a case in which the frequency separator 10 having a non-axisymmetric structure including the two bodies 161 and 162 arranged to be spaced apart from each other is described above, the exemplary embodiments are not limited thereto, and the frequency separator 160 may also include three or more bodies. Furthermore, according to other exemplary embodiments, the bodies may be connected to one another via three or more connecting members. The non-axisymmetric structures described above are merely examples, and the frequency separator according to exemplary embodiments may include various other types of non-axisymmetric structures for making bending moments of inertia in the two axial directions different from each other.

As described above, in the fiber scanning optical probe 100 according to the exemplary embodiments, the frequency separators 140, 150 and 160 including the various types of non-axisymmetric structures for making bending moments of inertia in the two axial directions different from each other are arranged on a portion of the optical fiber 120 between the actuator 110 and the mass 130, and thus, a resonance frequency in the two axial directions may be different from each other. Therefore, an occurrence of a coupling event between the two axial directions may be prevented. As a result, a precise scanning operation may be performed along a desired path, and thus, quality of an image obtained by a medical imaging apparatus may be improved.

Figure 7:
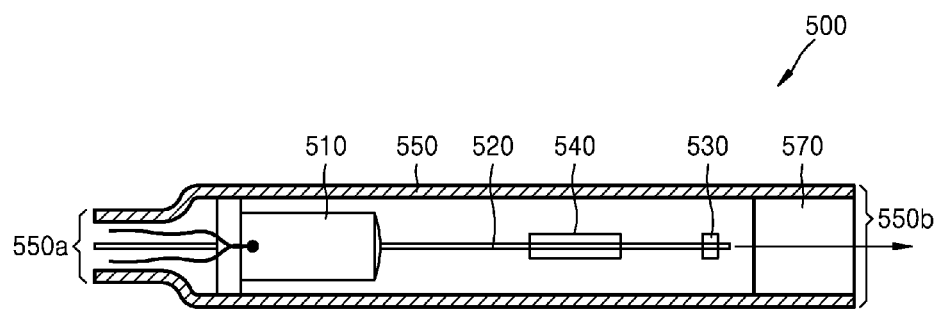
FIG. 7 is a diagram showing a fiber scanning optical probe according to another exemplary embodiment.

FIG. 7 is a diagram showing a fiber scanning optical probe 500 according to another exemplary embodiment.

Referring to FIG. 7, the fiber scanning optical probe 500 includes a probe housing 550 including a light input unit 550a and a light output unit 550b, and an optical fiber 520, an actuator 510, a mass 530, a frequency separator 540, and a lens unit 570 that are arranged inside the probe housing 550. The optical fiber 520 is driven by the actuator 510, delivers light incident via the light input unit 550a from an external light source to a target object, and may include single mode optical fibers. The actuator 510 may drive the optical fiber 520, such that the optical fiber 520 can be deformed in two axial directions. For example, the actuator 510 may be a piezoelectric actuator using a piezoelectric material that is deformed due to an electric signal. Since the detailed description of the actuator 510 has been provided above in relation to the above-described exemplary embodiments, detailed descriptions thereof will be omitted.

The mass 530 is arranged at a side of the optical fiber 520, where a through hole (not shown) may be formed in the mass 530 in which the optical fiber 520 passes. The mass 530 controls resonance frequency of the optical fiber 520 and may have the same cross-sectional shapes in two axial directions. Since the detailed description of the mass 530 has been provided above in relation to the above-described exemplary embodiments, detailed descriptions thereof will be omitted. The frequency separator 540 is arranged on a portion of the optical fiber 520 between the actuator 510 and the mass 530 and separates resonance frequencies in the two axial directions to be different from each other. The frequency separator 540 may include a non-axisymmetric structure for making bending moments of inertia in the two axial directions different from each other. To this end, the non-axisymmetric structure may have cross-sectional shapes different from each other in the two axial directions. The non-axisymmetric structure may be implemented as any of the non-axisymmetric structures described above with respect to the frequency separators 140, 150, and 160 shown in FIGS. 4 through 6, or may be any other of various types of non-axisymmetric structures. Since the detailed description of the non-axisymmetric structure have been provided above in relation to the above-described exemplary embodiments, detailed descriptions thereof will be omitted.

The lens unit 570 including at least one lens (not shown) is arranged on a light traveling path between an end portion of the optical fiber 520 and the light output unit 550b. The lens unit 570 concentrates a light transmitted via the optical fiber 520 to a target object. For example, the lens unit 570 may include an optical lens formed of a polymer material or a glass material, or may include a graded index (GRIN) lens having a refraction index distribution capable of concentrating light, for example.

Figure 8:
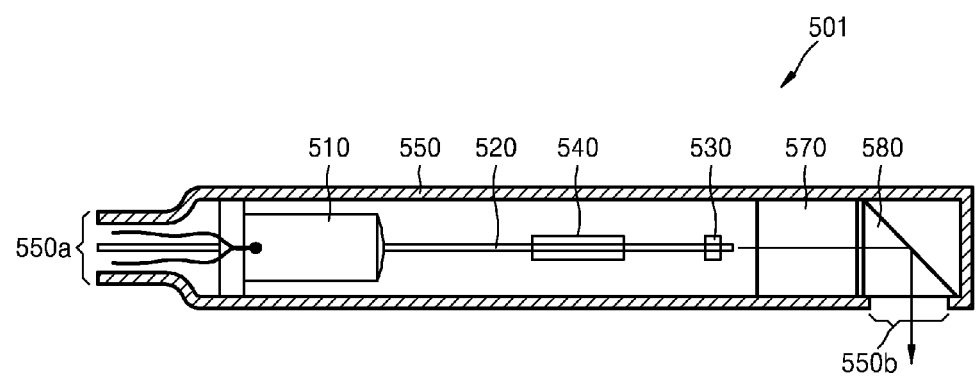
FIG. 8 is a diagram showing a fiber scanning optical probe according to another exemplary embodiment.

FIG. 8 is a diagram showing a fiber scanning optical probe 501 according to another exemplary embodiment. Descriptions below will focus on differences between the present exemplary embodiment of FIG. 8 and the previously described exemplary embodiments.

Figure 9:
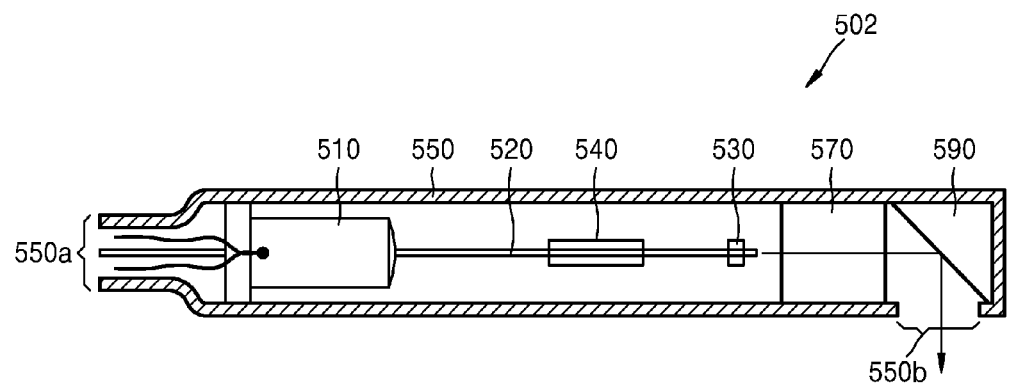
FIG. 9 is a diagram showing a fiber scanning optical probe according to another exemplary embodiment.

Referring to FIG. 8, the fiber scanning optical probe 501 includes the probe housing 550 including the light input unit 550a and the light output unit 550b, and the optical fiber 520, the actuator 510, the mass 530, the frequency separator, the lens unit 570, and a light traveling path changing member 580 that are arranged inside the probe housing 550. Since the optical fiber 520, the actuator 510, the mass 530, the frequency separator 540, and the lens unit 570 may be identical to those in the previously described exemplary embodiments, detailed descriptions thereof will be omitted. The light traveling path changing member 580 is arranged on a light traveling path between the lens unit 570 and the light output unit 550b, and changes a light traveling path of light incident from the lens unit 570. According to the present exemplary embodiment, the light traveling path changing member 580 may be implemented as a prism, where a light traveling path is changed due to total reflection inside the prism. FIG. 9 is a diagram showing a fiber scanning optical probe 502 according to another exemplary embodiment. The fiber scanning optical probe 502 shown in FIG. 9 is identical to the fiber scanning optical probe 501 of FIG. 8 except that a reflection mirror is used as a light traveling path changing member 590.

Figure 10:
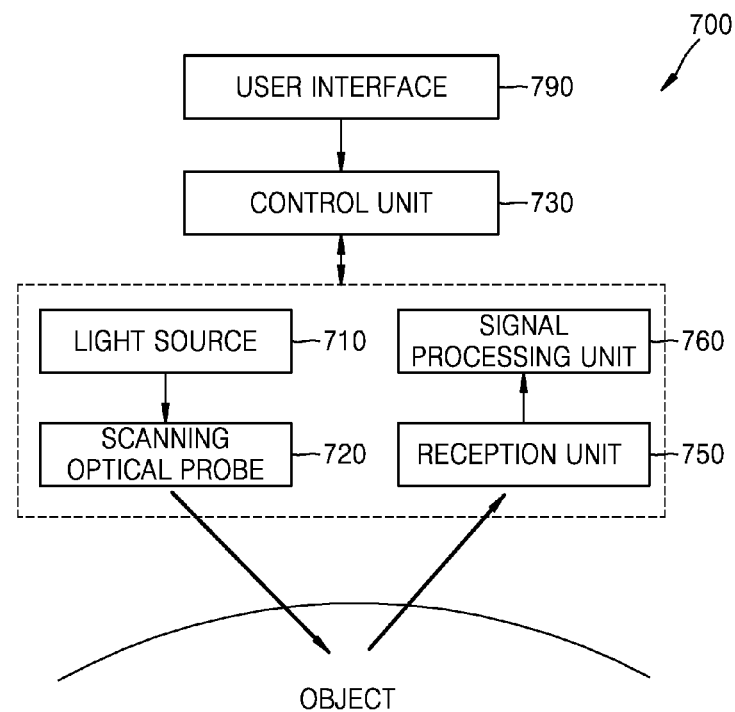
FIG. 10 is a schematic block diagram showing a medical imaging apparatus according to another exemplary embodiment.

FIG. 10 is a schematic block diagram showing a medical imaging apparatus 700 according to another exemplary embodiment.

Referring to FIG. 10, the medical imaging apparatus 700 includes a light source 710, a scanning optical probe 720 which scan-irradiates light from the light source 710 to a target object, a reception unit 750 (e.g., receiver) which receives a signal generated by the target object, and a signal processing unit 760 (e.g., signal processor) which generates an image signal by processing the signal received by the reception unit 750. The scanning optical probe 720 has a configuration for scanning a region of the target object and irradiating a light thereto. For example, the scanning optical probe 720 may be implemented as any one of the fiber scanning optical probes 100, 500, 501, or 502, or a combination thereof.

When light is irradiated to the target object by the scanning optical probe 720, a signal including property information regarding the target object is generated, and the reception unit 750 receives the signal. According to an exemplary embodiment, the reception unit 750 may be included in the scanning optical probe 720. The signal processing unit 760 generates an image signal by processing the signal received by the reception unit 750. Furthermore, the medical imaging apparatus 700 may further include a user interface 790 and a control unit 730. The user interface 790 may include an input unit and a display unit, and inputs (e.g., user instructions) may be transmitted to the control unit 730 via the user interface unit 790. Furthermore, the control unit 730 controls components constituting the medical imaging apparatus 700 according to an instruction input via the user interface unit 790. For example, the control unit 730 may control a scanning operation of the scanning optical probe 720. The control unit 530 may be embodied as a microprocessor, for example.

Components of the medical imaging apparatus 700 according to the present exemplary embodiment may be configured to use various types of methods, such as optical coherence tomography (OCT), optical coherence microscopy (OCM), or photoacoustic tomography (PAT). For example, based on types of signals generated by a target object, different detecting sensors may be arranged in the reception unit 750, and the signal processing unit 760 may process received signals via a corresponding method. For example, in case of using the PAT method, the light source 710 may be a pulse laser which induces ultrasound waves from a target object, and the reception unit 750 may be configured as an ultrasound reception unit including transducers for converting ultrasound waves generated by the target object into electric signals.

In a fiber scanning optical probe according to exemplary embodiments, a frequency separator including a non-axisymmetric structure for making bending moments of inertia in two axial directions different from each other is arranged on a portion of an optical fiber between an actuator and a mass, and thus, resonance frequencies in the two axial directions may become different from each other. Therefore, an occurrence of a coupling effect between the two axial directions may be prevented, and thus, a precise scanning operation may be performed along a desired path. As a result, the quality of an image obtained by a medical imaging apparatus may be improved. It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the exemplary embodiments as defined by the following claims.

What is claimed is:

1. A fiber scanning optical probe comprising:
   an optical fiber;
   an actuator attached onto the optical fiber and configured to drive the optical fiber at a driving resonance frequency;
   a mass attached to the optical fiber and configured to control the driving resonance frequency; and
   a frequency separator which is disposed between the actuator and the mass, and through which the optical fiber passes, the frequency separator being configured to separate the driving resonance frequency into separate resonance frequencies.

2. The fiber scanning optical probe of claim 1, wherein the actuator is configured to drive the optical fiber in two axial directions, and
   the frequency separator is configured to separate the resonance frequencies in the two axial directions to be different from each other.

3. The fiber scanning optical probe of claim 2, wherein the frequency separator is configured to control bending moments of inertia in the two axial directions to be different from each other.

4. The fiber scanning optical probe of claim 3, wherein the frequency separator comprises a non-axisymmetric structure having different cross-sectional shapes in the two axial directions.

5. The fiber scanning optical probe of claim 1, wherein the frequency separator comprises a through-hole through which the optical fiber passes.

6. The fiber scanning optical probe of claim 4, wherein the non-axisymmetric structure is formed of a single body of a cuboid.

7. The fiber scanning optical probe of claim 4, wherein the non-axisymmetric structure comprises a first body and a second body that is spaced apart from the first body, and the optical fiber is configured to pass through the first body and the second body.

8. The fiber scanning optical probe of claim 7, further comprising at least one connecting member interconnecting the first body and the second body.

9. The fiber scanning optical probe of claim 4, wherein the non-axisymmetric structure comprises silicon, a polymer, or a metal.

10. The fiber scanning optical probe of claim 2, wherein the mass has a same cross-sectional shape in the two axial directions.

11. The fiber scanning optical probe of claim 1, wherein the actuator comprises a piezoelectric actuator.

12. The fiber scanning optical probe of claim 1, further comprising a probe housing comprising:
    a light input unit configured to input light into the optical fiber; and
    a light output unit configured to output the light from the optical fiber,
    wherein the optical fiber, the actuator, and the frequency separator are provided in the probe housing.

13. The fiber scanning optical probe of claim 12, further comprising a lens unit provided inside the probe housing on a light traveling path between the light input unit and the light output unit, the lens unit comprising at least one lens.

14. The fiber scanning optical probe of claim 13, further comprising a light traveling path changing member which is provided between the lens unit and the light output unit.

15. The fiber scanning optical probe of claim 14, wherein the light traveling path changing member comprises a prism.

16. The fiber scanning optical probe of claim 14, wherein the light traveling path changing member comprises a reflection mirror.

17. A medical imaging apparatus comprising:
    a light source configured to irradiate light;
    a fiber scanning optical probe configured to scan a target object by using the light from the light source;
    a receiver configured to receive a signal from the target object; and
    a signal processor configured to generate an image signal by processing the signal received by the receiver,
    wherein the fiber scanning optical probe comprises:
       an optical fiber;
       an actuator attached onto the optical fiber and configured to drive the optical fiber at a driving resonance frequency;
       a mass attached to the optical fiber and configured to control the driving resonance frequency; and
       a frequency separator which is disposed between the actuator and the mass, through which the optical fiber passes, and which is configured to separate the driving resonance frequency into separate resonance frequencies.

18. The medical imaging apparatus of claim 17, wherein the actuator is configured to drive the optical fiber in two axial directions, and
   the frequency separator is configured to separate the resonance frequencies in the two axial directions to be different from each other.

19. The medical imaging apparatus of claim 18, wherein the frequency separator comprises a non-axisymmetric structure having different cross-sectional shapes in the two axial directions.

20. The medical imaging apparatus of claim 17, wherein the signal processed by the signal processor is a signal generated according to one of optical coherence tomography (OCT), optical coherence microscopy (OCM), or photoacoustic tomography (PAT).

21. An optical probe, comprising:
   an optical fiber configured to guide light;
   an actuator configured to deform the optical fiber by generating a resonance frequency, to thereby control a direction of the guided light; and
   a device configured to control two bending moments of inertia respectively corresponding to two axial directions of the optical fiber such that the two bending moments of inertia are different from each other,
   wherein the device comprises a non-axisymmetric structure having different respective cross-sectional shapes in the two axial directions that are perpendicular to each other.

* * * * *